(12) United States Patent
Kibble et al.

(10) Patent No.: US 10,854,328 B2
(45) Date of Patent: Dec. 1, 2020

(54) UNIVERSAL WEB SERVICE FOR DICOM OBJECTS

(71) Applicant: FUJIFILM MEDICAL SYSTEMS U.S.A., INC., Stamford, CT (US)

(72) Inventors: Gary Kibble, Cary, NC (US); Peter Jakes, Stamford, CT (US)

(73) Assignee: FUJIFILM MEDICAL SYSTEMS U.S.A., INC., Stamford, CT (US)

( * ) Notice: Subject to any disclaimer, the term of this patent is extended or adjusted under 35 U.S.C. 154(b) by 0 days.

(21) Appl. No.: 16/370,366

(22) Filed: Mar. 29, 2019

(65) Prior Publication Data

US 2020/0312440 A1    Oct. 1, 2020

(51) Int. Cl.
*G16H 30/20* (2018.01)
*G06F 16/955* (2019.01)
*G06F 16/25* (2019.01)
*G06F 40/221* (2020.01)

(52) U.S. Cl.
CPC ........... *G16H 30/20* (2018.01); *G06F 16/252* (2019.01); *G06F 16/9566* (2019.01); *G06F 40/221* (2020.01)

(58) Field of Classification Search
None
See application file for complete search history.

(56) References Cited

U.S. PATENT DOCUMENTS

| 8,813,024 B2 | 8/2014 | Akkiraju et al. |
| 9,704,094 B2 | 7/2017 | Amir et al. |
| 2005/0154289 A1 | 7/2005 | Judd et al. |

(Continued)

FOREIGN PATENT DOCUMENTS

| EP | 3451342 | 3/2019 |
| WO | 2016090326 | 6/2016 |

OTHER PUBLICATIONS

Varun Goyal, System and Method for Integrating and Processing of Information from Plurality of Sources, India, Jun. 30, 2015, 42 pages.

(Continued)

*Primary Examiner* — Cai Y Chen
(74) *Attorney, Agent, or Firm* — Heslin Rothenberg Farley & Mesiti P.C.

(57) ABSTRACT

A universal service for objects (e.g., DICOM objects) and method for processing the same are described. In one embodiment, the method comprises: receiving, at a web service engine, a web services request from a remote web client for one or more Digital Imaging and Communications in Medicine (DICOM) objects; generating a DICOM Message Service Element (DIMSE) request from the web services request, wherein generating the DIMSE service request includes parsing a modified base URL that includes information for a DIMSE service request, the modified URL being compliant with a standard that specifies a web-based service for accessing and presenting DICOM objects; sending the DIMSE service request to a server; receiving a response to the DIMSE service request from the server; reformatting the response to be compliant with the standard that specifies a web-based service for accessing and presenting DICOM objects; and returning the reformatted response to the remote web client.

23 Claims, 10 Drawing Sheets

(56) References Cited

U.S. PATENT DOCUMENTS

2009/0274384 A1* 11/2009 Jakobovits ............ G06F 19/321
 382/254
2014/0142984 A1* 5/2014 Wright ................... G16H 30/20
 705/3
2014/0143299 A1 5/2014 Klotzer
2017/0195382 A1 7/2017 Lingley
2017/0255452 A1 9/2017 Barnes et al.
2018/0247707 A1 8/2018 Westin et al.
2019/0065763 A1* 2/2019 Berg ...................... G16H 30/20

OTHER PUBLICATIONS

International Search Report for Application No. PCT/US2020/020522 dated Jul. 2, 2020, 13 pages.

* cited by examiner

UNIVERSAL WEB SERVICE FOR DICOM OBJECTS

FIELD OF THE INVENTION

Embodiments of the present invention relate to the field of medical image retrieval, querying and storage; more particularly, embodiments of the present invention relate to processing web services requests related to Digital Imaging and Communications in Medicine (DICOM) objects.

BACKGROUND

Physicians and other medical personnel often review all of a patient's relevant clinical information when making healthcare decisions. The clinical information is typically included in healthcare studies and structured reports. These often include information about a patient's history, diagnostic reports from different domains, images, and other clinical data in electronic format.

The medical images and imaging reports are often stored as DICOM objects. The healthcare studies are typically generated in response to a physician ordering an examination for their patient. The examination is performed and the generated study is often sent to a Picture Archiving and Communication System (PACS).

In 2003 the National Electrical Manufacturers Association (NEMA) published a web services standard for accessing and presenting DICOM objects (e.g., images, medical imaging reports). More specifically, the standard provides a mechanism for accessing a DICOM object using the HTTP/HTTPS protocol. Many vendors support the NEMA DICOM Web Service Standard. For example, WADO-RS provides the ability to download one or more DICOM objects via the Internet, QIDO-RS provides the ability to query for DICOM objects via the Internet, STOW-RS provides the ability to send DICOM objects for remote storage via the Internet, and WADO-URI, an older version of WADO-RS, provides the ability to download a single DICOM object per Internet request. The current version of the standard can be found at:
   http://dicom.nema.org/medical/dicom/current/output/
      chtml/part18/PS3.18.html When NEMA published the standard for Web Services for DICOM, the expectation was for each PACS vendor to build their own implementation of the standard specified web services to provide Internet access to their PACS. The standard has been very successful, but for a DICOM client (Service Class User or SCU) that wants to use WADO-RS/QIDO-RS as its sole communication interface, there will be some PACS that cannot be accessed due to lack of vendor support, or non-standard WADO-RS/QIDO-RS implementation, or custom web authentication requirements.

Vendors that support these web services provide access only their own vendor specific PACS. For example, the AGFA® WADO-RS must be used to download from an AGFA® PACS and the FUJIFILM WADO-RS must be used to download from the Synapse® PACS. There are no vendors with a WADO-RS/QIDO-RS that can access any DICOM PACS.

SUMMARY OF THE INVENTION

A universal web service for objects (e.g., DICOM objects) and method for processing the same are described. In one embodiment, the method comprises: receiving, at a web service engine, a web services request from a remote web client for one or more Digital Imaging and Communications in Medicine (DICOM) objects; generating a DICOM Message Service Element (DIMSE) request from the web services request, wherein generating the DIMSE service request includes parsing a modified base URL that includes information for a DIMSE service request, the modified URL being compliant with a standard that specifies a web-based service for accessing and presenting DICOM objects; sending the DIMSE service request to a server; receiving a response to the DIMSE service request from the server; reformatting the response to be compliant with the standard that specifies a web-based service for accessing and presenting DICOM objects; and returning the reformatted response to the remote web client.

In another embodiment, a medical image management system comprises a network interface to communicate with one or more clients and one or more remote servers and an access engine, having circuitry, to receive a first set of requests from the one or more clients that are directed to the one or more remote servers, and to issues a second set of requests to the remote servers in response to the first set of requests, where the second set of requests is either a DICOM web service request or a DIMSE request.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

DETAILED DESCRIPTION

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

Embodiments of the present invention are directed to systems and methods for accessing DICOM objects. The DICOM objects may be stored in a PACS, VNA, or other server. In one embodiment, the DICOM objects are part of healthcare studies. In one embodiment, the access is provided through a single, universal DICOM web interface. In one embodiment, the universal DICOM web interface is NEMA compliant and is able to access any DICOM PACS or server that authorizes a DICOM client (e.g., Service Class User's (SCU's)) application entity title (AeTitle or AET). The embodiments disclosed herein provide one or more of the following advantages. For example, embodiments allow for a single client/SCU internet authentication regardless of which vendor PACS is being used, provides a consistent DICOM web services implementation regardless of vendor PACS, no requirement for the client/SCU to support DICOM C-FIND/C-MOVE/C-GET/C-STORE protocol, and enables Internet access to PACS vendors not yet supporting DICOM web services. For purposes herein, SCU is used to describe a client, including, but not limited to, a DIMSE message (TCP) client or a Web client. Having briefly described an overview of the present invention, embodiments of the invention will be discussed with reference to FIGS. 1-10.

The subject matter of embodiments of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies.

Having briefly described embodiments of the present invention, an exemplary operating environment suitable for use in implementing embodiments of the present invention is described below.

Figure 1:
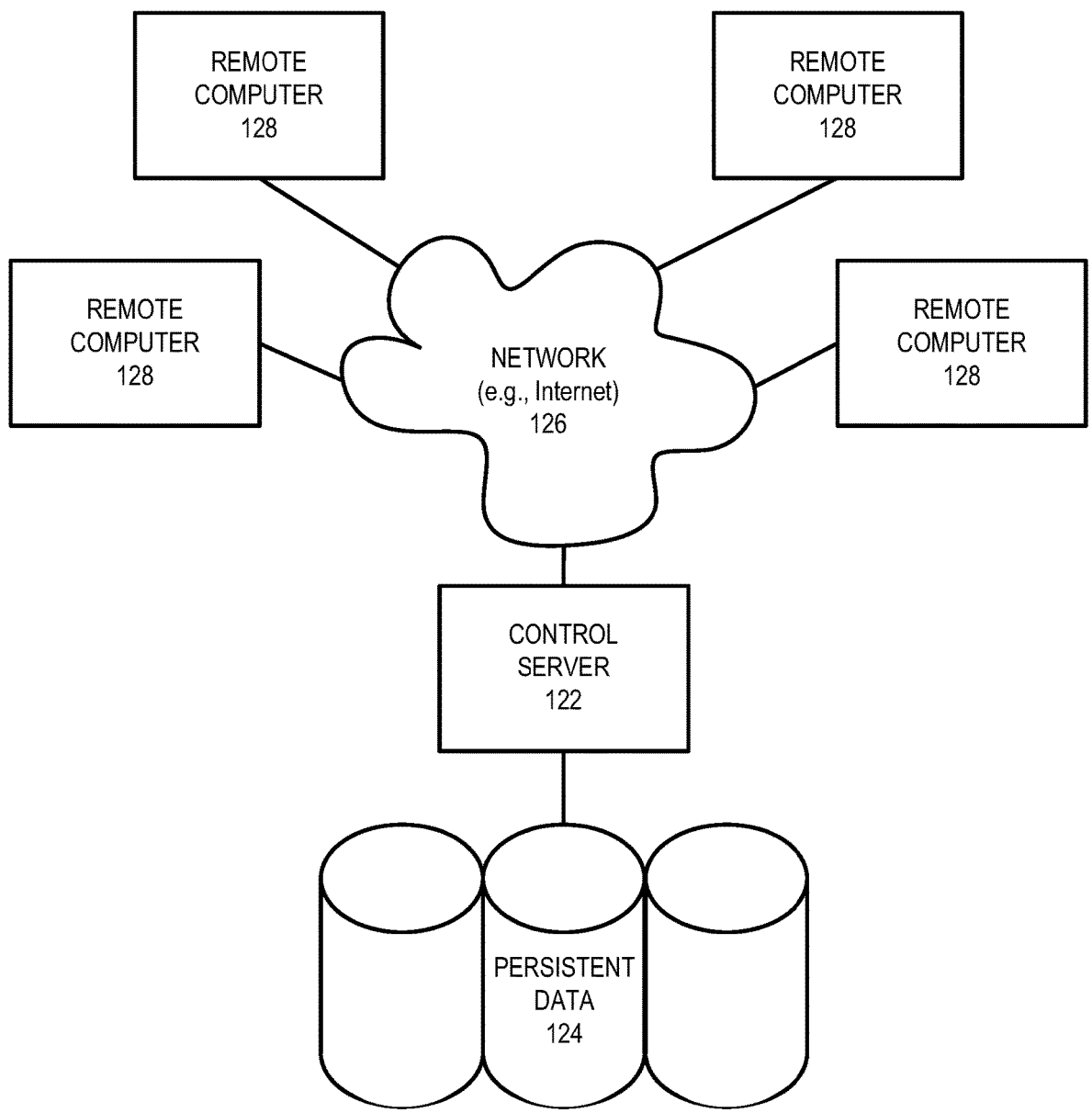
FIG. 1 illustrates an exemplary medical information computing system environment, with which embodiments of the present invention may be implemented.

Referring to the drawings in general, and initially to FIG. 1 in particular, a medical information computing system environment, with which embodiments of the present invention may be implemented is illustrated and designated generally as reference numeral 120. It will be understood and appreciated by those of ordinary skill in the art that the illustrated medical information computing system environment 120 is merely an example of one suitable computing environment and is not intended to suggest any limitation as to the scope of use or functionality of the invention. Neither should the medical information computing system environment 120 be interpreted as having any dependency or requirement relating to any single component or combination of components illustrated therein.

Embodiments of the present invention may be operational with numerous general-purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in association with local and/or remote computer storage media including, by way of example only, memory storage devices.

With continued reference to FIG. 1, the exemplary medical information computing system environment 120 includes a general-purpose computing device in the form of a control server 122. Components of control server 122 may include, without limitation, a processing unit, internal system memory, and a suitable system bus for coupling various system components, including Persistent Storage 124, with control server 122. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Control server 122 typically includes therein, or has access to, data stored in a variety of computer-readable media, for instance, Persistent Storage 124. Computer-readable media can be any available media that may be accessed by server 122, and includes volatile and nonvolatile media, as well as removable and non-removable media. By way of example, and not limitation, computer-readable media may include computer storage media. Computer storage media may include, without limitation, volatile and nonvolatile media, as well as removable and non-removable media implemented in any method or technology for storage of information, such as computer-readable instructions, data structures, program modules, data bases, formatted files, registry keys, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by control server 122. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including Persistent Storage 124, provide storage of computer-readable instructions, data structures, program modules, and other data for control server 122. Control server 122 may operate in a computer network 126 using logical connections to one or more remote computers 128. Remote computers 128 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as intensivists, surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, radiologic technologists, researchers, veterinarians, students, and the like. Remote computers 128 may also be physically located in non-traditional medical care environments so that the entire health care community may be capable of integration on the network. Remote computers 128 may be personal computers, servers, routers, network PCs, peer devices, personal digital assistants, other common network nodes, or the like, and may include some or all of the elements described above in relation to control server 122. For example and not by way of limitation, control server 122 could reside on the remote computers 128 as local software without network 126.

Exemplary computer networks 126 may include, without limitation, local area networks (LANs) and/or wide area networks (WANs). Such networking environments are commonplace in offices, enterprise-wide computer networks, intranets, and the Internet. When utilized in a WAN networking environment, the control server 122 may include a modem or other means for establishing communications over the WAN, such as the Internet. In a networked environment, program modules or portions thereof may be stored in association with control server 122, the Persistent Storage 124, or any of remote computers 128. For example, and not by way of limitation, various application programs may reside on the memory associated with any one or more of remote computers 128. It will be appreciated by those of ordinary skill in the art that the network connections shown are exemplary and other means of establishing a communications link between the computers (e.g., control server 122 and remote computers 128) may be utilized.

In operation, a clinician may enter commands and information into control server 122 or convey the commands and information to control server 122 via one or more of remote computers 128 through input devices, such as a keyboard, a pointing device (commonly referred to as a mouse), a trackball, or a touch pad. Other input devices may include, without limitation, microphones, scanners, or the like. Commands and information may also be sent directly from a remote healthcare device to the control server 122. In addition to a monitor, control server 122 and/or remote computers 128 may include other peripheral output devices, such as speakers and a printer.

Although many other internal components of control server 122 and remote computers 128 are not shown, those of ordinary skill in the art will appreciate that such components and their interconnection are well known. Accordingly, additional details concerning the internal construction of control server 122 and remote computers 128 are not further disclosed herein.

Figure 2:
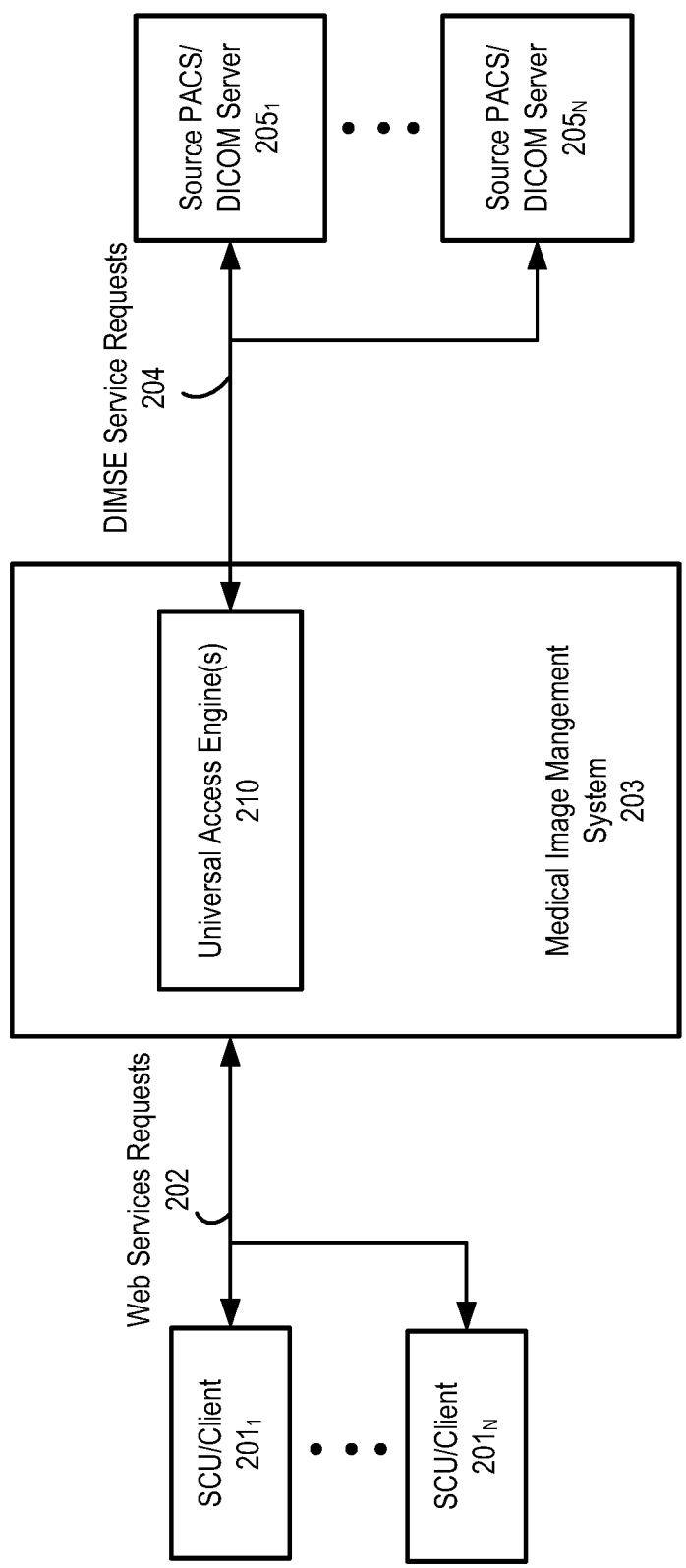
FIG. 2 shows an example of a computing system architecture for accessing DICOM objects.

With reference to FIG. 2, a block diagram is illustrated that shows an example of a computing system architecture for handling universal web services for Digital Imaging and Communications in Medicine (DICOM) objects. It will be appreciated that the computing system architecture shown in FIG. 2 is merely an example of one suitable computing system and is not intended as having any dependency or requirement related to any single module/component or combination of modules/components.

Referring to FIG. 2, SCU (client) $201_1$-SCU (client) $201_N$ generate web services requests 202 that are sent to medical image management system 203. In one embodiment, SCU (client) $201_1$-SCU (client) $201_N$ comprise remote web clients for viewing, querying or storing medical images. A universal access engine(s) 210 operates as a web services engine and receives web services request 202 from SCU (client) $201_1$-SCU (client) $201_N$. In one embodiment, the web services request comprises QIDO-RS, WADO-RS, STOW-RS, or WADO-URI requests. However, the web services requests are not limited to these requests and may include future DICOM web services approved by NEMA, DICOM or IHE. In another embodiment, the web services request uses a URL that can be converted by access engine 210 into either a DICOM web service request (like QIDO-RS) or into a DICOM Message (DIMSE) request like C-FIND. In yet another embodiment, access engine 210 runs as an application on the SCU/client devices and a software interface is used to issue requests which can be implemented by access engine 210 as either a DICOM web service request or a DICOM Message (DIMSE) request. Thus, in this case, the service is a local process accessible to a medical imaging client which acts as a switch board for web services to one or more remote medical data systems like a PACS or VNA, and this switchboard issues DICOM web requests when supported by the remote PACS/VNA and otherwise uses DIMSE services as described above with the response converted to DICOM web services formats for client use.

In one embodiment, the web services request 202 is for a PACS 205 that does not support DICOM web services, or supports DICOM web services in a way that is non-standard or supports it in a way that is difficult for SCU 201 to authenticate with. When any of these conditions apply, then in response to receiving the web services request, the universal access engine 210 generates a DIMSE service request. In one embodiment, the DEVISE service request comprises a C-FIND, C-GET, C-MOVE or C-STORE operation. In one embodiment, the universal access engine 210 generates a DEVISE service request based upon a Source PACS 205 identifier embedded within the web service request 202. In one embodiment, the web service request 202 includes additional information necessary for a DICOM C-FIND, C-GET, C-MOVE or C-STORE request such as one or more of SCU AeTitle, Source PACS AeTitle, Source PACS Host and Port. In one embodiment, the web service request 202 is parsed by the access engine 210 to identify a type of web service (e.g. QIDO-RS), create a DICOM client, and have the DICOM client issue one DIMSE service request based on the type of web service that was identified. In one embodiment, the DIMSE service request that is generated is compliant with the standard that specifies DICOM messaging for accessing DICOM objects. In one embodiment, the standard is the NEMA DICOM PS3.1.

Universal access engine 210 sends the DIMSE service request 204 to a source PACS, DICOM server or VNA, such as source PACS/DICOM server $205_1$-source PACS/DICOM server $205_N$. The source PACS generates a response to the DIMSE service request and sends the response to universal access engine 210. Universal access engine 210 reformats the response into a format that the remote web client understands and returns the reformatted response to the remote web client, such as SCU (client) $201_1$-SCU (client) $201_N$.

Figure 3:
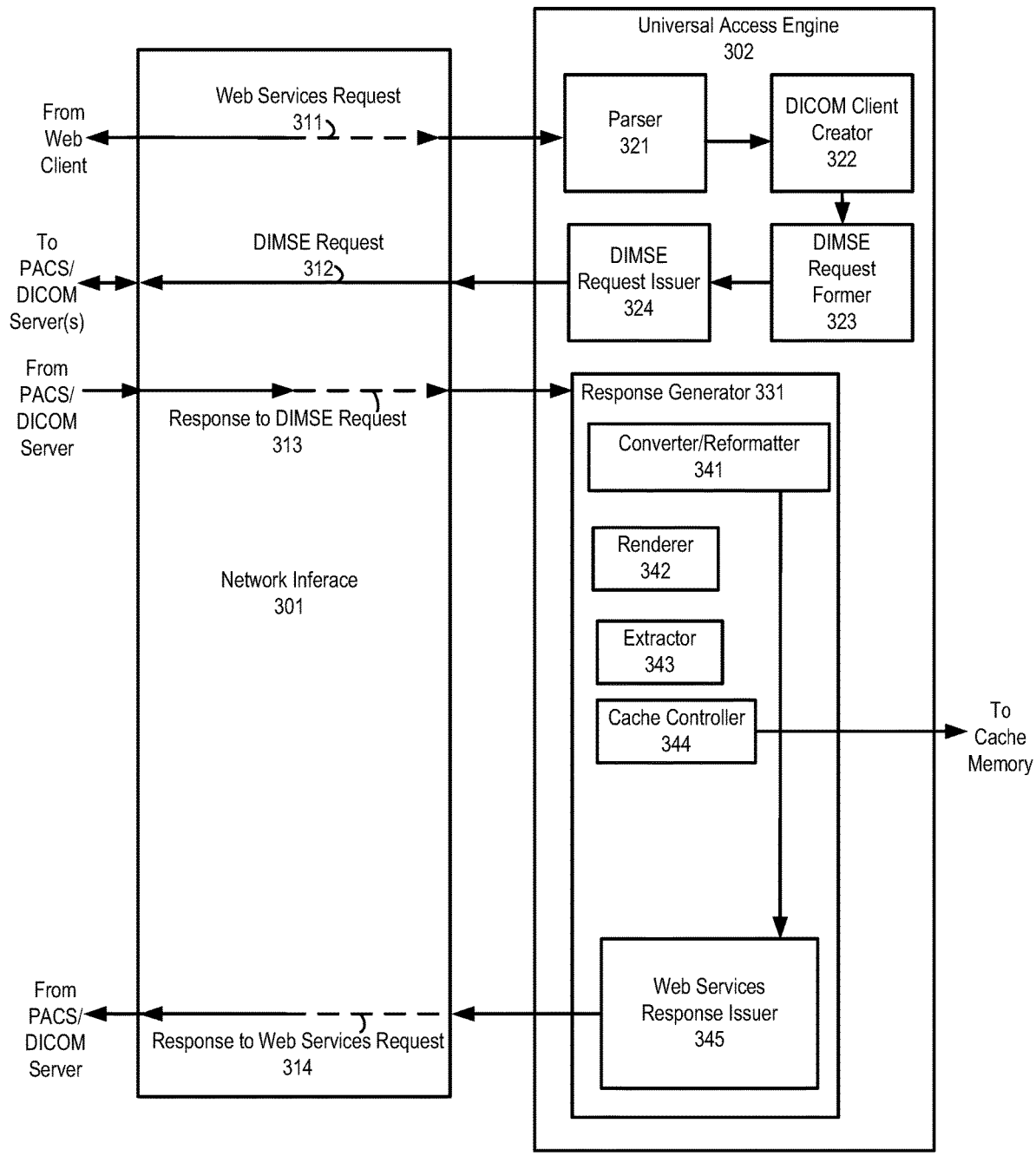
FIG. 3 a block diagram of a portion of one embodiment of a medical image management system for handling web services requests.

FIG. 3 is a block diagram of a portion of one embodiment of a medical image management system for handling web services requests, including a network interface 301 and universal access engine 302. In one embodiment, universal access engine 302 comprises one or more processors or other hardware (circuitry, dedicated logic, etc.), software (e.g., software running on a chip), firmware, or a combination of the three.

Referring to FIG. 3, a web service request 311 is received by network interface 301 from a web client. Web services request 311 is sent to the universal access engine 302 where a parser 321 parses the web service's request to determine the type of request. In response to determining the type of request, DICOM client generator 322 generates a DICOM SCU client. There are third party libraries such as, for example, MultiTech msiCOM3, that can provide SCU client software or from which one skilled in the art can build their own SCU client. Also based on the type of web services request, a DIMSE request former 323 generates, or otherwise forms, a DIMSE request. In one embodiment, the DIMSE request comprises a DICOM object for a C-FIND, C-GET, C-MOVE or C-STORE operation. Responsive to the DIMSE request former 323 generating a DIMSE request object, DIMSE request issuer 324 issues DIMSE request 312. In one embodiment, DIMSE request issuer 324 issues DIMSE request 312 to network interface 301 which takes DIMSE request 312 and sends over a network (e.g., the Internet, etc.) to the PACS/DICOM/VNA server identified by the parser 321.

Subsequently, the PACS/DICOM/VNA server that received the DIMSE request generates a DIMSE response 313 to DIMSE request 312, which is received by network interface 301 of the medical image management system. Response 313 to DIMSE request is sent to Response generator 331 of universal access engine 302. In response to response 313, a converter/reformatter 341 converts and/or reformats response 313 to a format that is compliant with web services request. For example and not by way of limitation, a C-FIND response may be converted to application/dicom+xml or application/dicom+json as specified in the NEMA standard PS3.18 for QIDO-RS. Optionally, the response generator 331 may render DICOM objects for display using renderer 342 if, for example, the web service request requires a JPEG or PNG response. Optionally, the response generator 331 may extract bulk data from the DIMSE request response 313 using extractor 343 to satisfy a WADO-RS web service request for bulk data. Optionally, the response generator 331 may convert DICOM header information and create a metadata response using extractor 343 to satisfy a WADO-RS metadata web service request. Optionally the DIMSE response 313, or parts of it or elements rendered from it, may be stored in cache memory using cache controller 344. In one embodiment the cache memory is used instead of the client creator 322 to access medical content when the web service request 311 is repeated.

After conversion/reformatting, the web services response is sent to web services response issuer 345 which issues web services response 314 to network interface 301, which sends it to the web client that originally generated web services request 311.

Figure 4A:
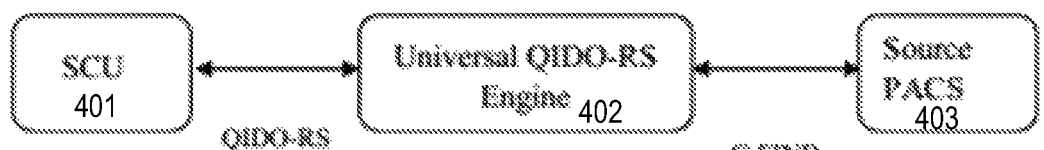
FIGS. 4A-4C illustrate the examples of the conversion of web service requests to DIMSE service requests.
Figure 4B:
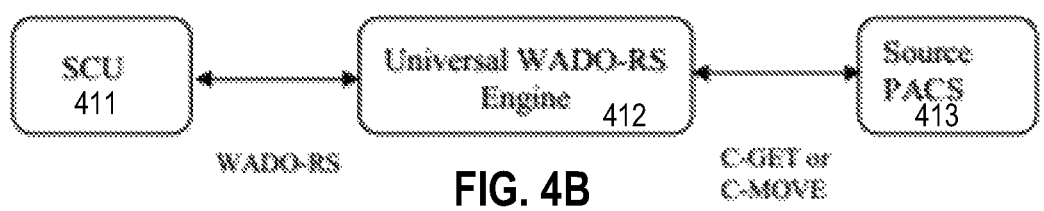
Figure 4C:
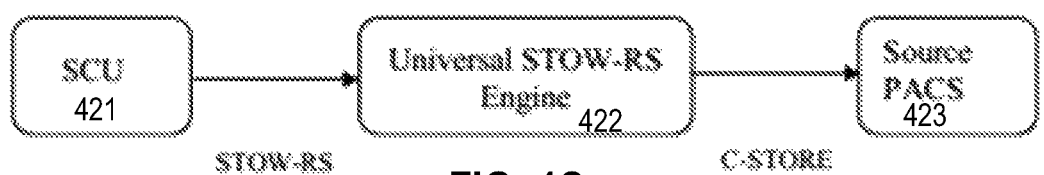

FIGS. 4A-4C illustrate examples of the conversion of web services requests to DIMSE service requests. Referring to FIG. 4A, SCU 401, which is a web client, generates a QIDO-RS web services request and sends it to a universal QIDO-RS engine 402, which converts it to a DIMSE C-FIND request that is sent to source PACS 403 (a DICOM server). In response to the DIMSE C-FIND request, source PACS 403 generates a response and sends the response to universal QIDO-RS engine 402, which reformats the response and sends it as a response to SCU 401.

Referring to FIG. 4B, SCU 411, which is a web client, generates a WADO-RS web services request and sends it to a universal WADO-RS engine 412, which converts it to a DIMSE C-GET or C-MOVE request that is sent to source PACS 413 (a DICOM server). In response to the DIMSE C-GET or C-MOVE request, source PACS 413 generates a response and sends the response to universal WADO-RS engine 412, which reformats the response and sends it as a response to SCU 411.

Referring to FIG. 4C, SCU 421, which is a web client, generates a STOW-RS web services request and sends it to a universal STOW-RS engine 422, which converts it to a C-STORE DIMSE request that is sent to source PACS 423 (a DICOM server). In response to the C-STORE DIMSE request, source PACS 423 generates a response and sends the response to universal STOW-RS engine 422, which reformats the response and sends it as a response to SCU 421.

The NEMA standard for DICOM Web Services (PS3.18) specifies the following URL formats for specific web server requests for studies of medical data:
QIDO-RS: {SERVICE}/studies
WADO-RS: {SERVICE}/studies/{StudyInstanceUID}
STOW-RS: {SERVICE}/studies[/{StudyInstanceUID}]
where {SERVICE} is the base URL for the service. This may be a combination of protocol (either http or https), host, port, and application. The definition of "application" is left open to the vendor. For example, a request to a VNA can look like this:
http://myVna:8080/wado-rs/MyCustomerDomain/studies
where MyCustomerDomain is part of the application name and specifies one of many content partitions on the VNA.

In one embodiment, one new feature of the universal access engine(s) disclosed herein is to extend the application name to include all the information necessary for a DICOM C-FIND/C-GET/C-MOVE/C-STORE request while remaining compliant with the DICOM Web Service Standard.

In one embodiment, calls to the universal access engine(s) define {SERVICE} are as follows:
QIDO-RS URL
http://<UniversalServer>/qido-rs/cfind/<SCU AET>/<SCP AET>/<SCP Host>/<SCP Port>/<Dest AET>
WADO-RS URL
http://<UniversalServer>/wado-rs/cmove/<SCU AET>/<SCP AET>/<SCP Host>/<SCP Port>/<Dest AET> or
http://<UniversalServer>/wado-rs/cget/<SCU AET>/<SCP AET>/<SCP Host>/<SCP Port>
STOW-RS URL
http://<UniversalServer>/stow-rs/cstore/<SCU AET>/<SCP AET>/<SCP Host>/<SCP Port>
where the protocol may be http or https, <UniversalServer> is a local web server implementing the universal access service, and qido-rs, wado-rs, stow-rs are optional service identifiers. In one embodiment, any unique keyword could be used to identify the server type, e.g. qido instead of qido-rs, or the service identifier can be omitted with additional parsing logic applied. In one embodiment, the service identifier is omitted and the service context is defined from the http request as follows:
  a http request using POST identifies STOW-RS.
  If the http request uses GET with no {StudyInstanceUID}, then assume QIDO-RS
  If the http request uses GET and {StudyInstanceUID} is present, then assume WADO-RS
For example, the following http get request with no StudyInstanceUID
http://<Universal Server>/<SCU AET>/<SCP AET>/<SCP Host>/<SCP Port>/<Dest AET>/Studies
is for QIDO-RS while the following URL with a StudyInstanceUID http://<Universal Server>/<SCU AET>/<SCP AET>/<SCP Host>/<SCP Port>/<Dest AET>/Studies/ 1.3.6.1.4.1.5962.1.3.1.1.20040826185059
is for WADO-RS.

In the above calls, cfind/cmove/cget/cstore are optional tags to allow the web services to toggle between the traditional DICOM web service usage versus the universal remote PACS access. For example, https://myServer/qido-rs/studies or https://myServer/studies can query the myServer PACS using QIDO-RS while https://myServer/qido-rs/cfind/aeA/aeB/Pacs/aeC/studies or https://myServer/cfind/aeA/aeB/Pacs/aeC/studies uses myServer to make a C-FIND request to a remote PACS aeB with the response reformatted for QIDO-RS.

If myServer is not a PACS or VNA web server, or DICOM web services for myServer PACS is not required or desired, the cfind/cmove/cstore tags can be omitted and a query could look like http://myServer/aeA/eeB/Pacs/aeC/studies (omitting the service identifier), or http://myServer/qido-rs/aeA/aeB/Pacs/aeC/studies (with service identifier).

In this embodiment, the universal access engine is solely a proxy to one or more independent Source PACS servers.

In the above calls, <SCU AET> is the calling AeTitle of the SCU. This can be used for authorization of DICOM request and may be required by a remote PACS.

Also, in the above calls, <SCP AET> is the called AeTitle of the remote PACS, <SCP Host> is the machine name of the remote PACS, and <SCP Port> is the DICOM port for the remote PACS. For example, Synapse® PACS uses port 104 by default for DIMSE requests.

In the above calls, <Dest AET> is the return address AeTitle used by C-MOVE. In one embodiment, this needs to be configured on the remote PACS to C-STORE requested content back to the Universal Web Service. Note that <Dest AET> is not strictly required for QIDO-RS using C-FIND. It is included here as a convenience since a proper QIDO-RS response should include a WADO-RS URL for accessing each DICOM instance found by the query. With the inclusion of <Dest AET>, this QIDO-RS has all the information needed to build a WADO-RS URL that supports C-MOVE. If the universal WADO-RS uses C-GET instead of C-MOVE, the <Dest AET> is not required in the URL.

QIDO-RS Workflow

In one embodiment, the QIDO-RS workflow begins after a QIDO-RS request is issued by a remote web client. When the universal web service engine described herein receives a QIDO-RS request or, upon parsing the parameters after {SERVICE} in the request, recognizes that the request is QIDO-RS, then the universal web service engine creates an internal DICOM SCU client that issues a C-FIND request to the <SCP Host> on the <SCP Port> using the AeTitles provided <SCU AET> and <SCP AET>. Subsequently, the SCP Host (e.g., PACS, VNA server, etc.) generates and sends back a C-FIND response. The universal web service engine converts the C-FIND response to DICOM+XML, or DCIOM+JSON as specified by the Accept type(s) of the initial web request and the NEMA DICOM Web Services standard. In one embodiment, DICMO-XML is the NEMA standard PS3.18 default if no Accept Type is specified. Optionally, in one embodiment, the universal web service engine also caches the response (formatted or native DICOM or custom) for faster response for repeated queries for the same DICOM objects in the future. The universal web service engine returns the re-formatted C-FIND response to the remote web client. In one embodiment, the QIDO-RS response is batched until all C-FIND messages are received and returned in one HTTP response of known size. In another embodiment, the response is streamed, during which a QIDO-RS formatted (DICMO-XML or DICMO-JSON) data chunk is returned after each C-FIND message is received.

Figure 5:
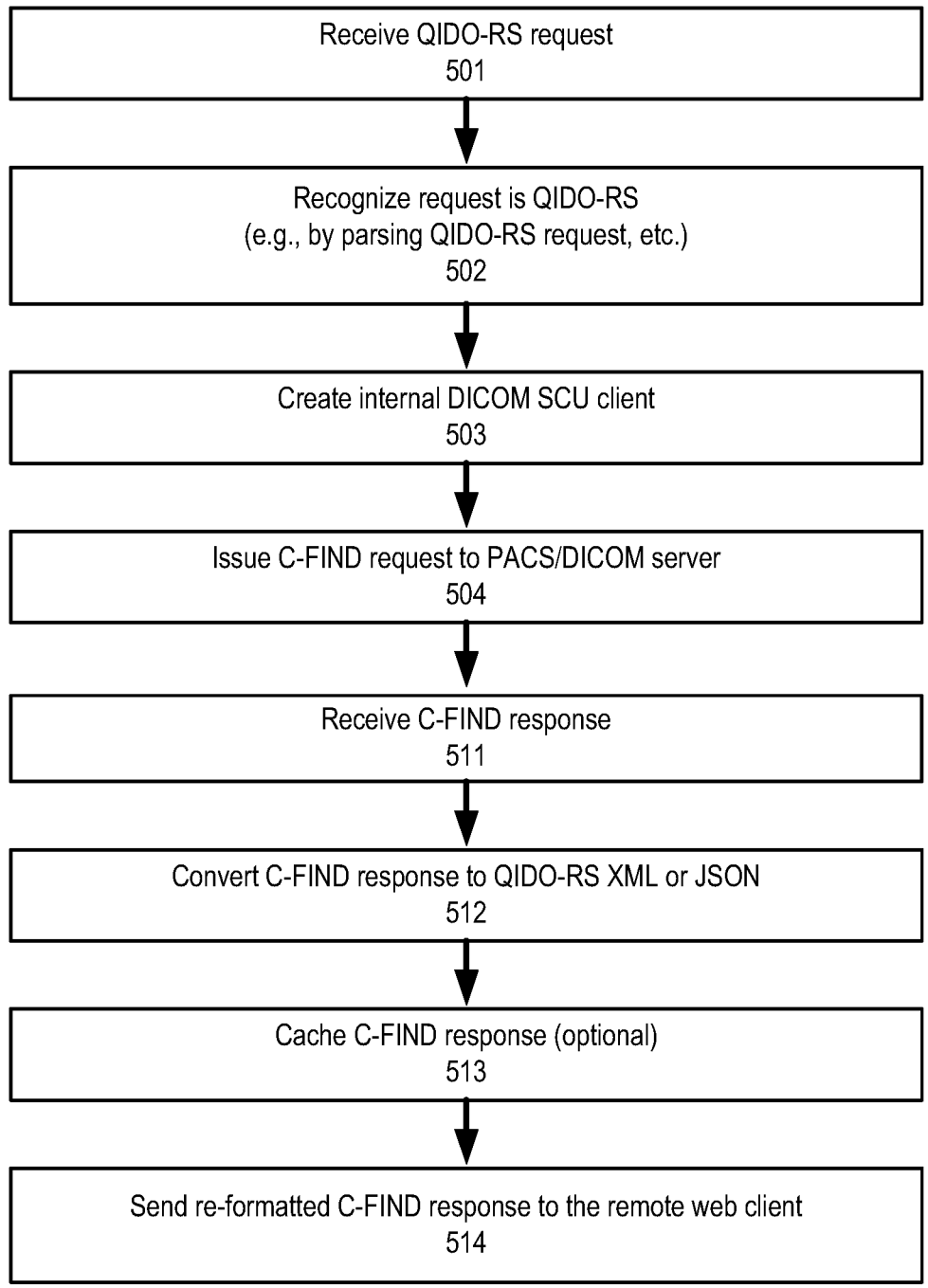
FIG. 5 is a flow diagram of one embodiment of a process for handling a QIDO-RS web services request.

FIG. 5 is a flow diagram of one embodiment of a process for handling a QIDO-RS request. In one embodiment, the process is performed by processing logic that may comprise hardware (circuitry, dedicated logic, etc.), software (e.g., software running on a chip), firmware, or a combination of the three. In one embodiment, the process is performed by a medical image management platform, such as, for example, but not limited to, the medical image management platforms described above in conjunction with FIGS. 2 and 3.

Referring to FIG. 5, the process begins by processing logic receiving a QIDO-RS request (processing block 501). In response to receiving the QIDO-RS request, processing logic recognizes the request is a QIDO-RS request (processing block 502). In one embodiment, processing logic recognizes the request as a QIDO-RS request by parsing the QIDO-RS request to find a service identifier. This parsing may occur within and after the {SERVICE} part of the QIDO-RS URL request.

After recognizing the request as a QIDO-RS request, processing logic creates an internal DICOM SCU client (processing block 503) by use of third party DICOM libraries or custom software. Such clients are well known to those in the art and specified under DICOM standard PS3.18.

After creation of the DICOM SCU client, the DICOM SCU client issues a C-FIND request to the PACS/VNA/DICOM server (e.g., SCP host) identified by the original QIDO-RS web services request (processing block 504).

Subsequently, processing logic receives a C-FIND response (processing block 511) and converts the C-FIND response to other formats such as, for example, NEMA standard PS3.18 DICOM+XML or DICOM+JSON (processing block 512). Alternative schemas of JSON, XML or other formats could be used to return results. In one embodiment, whether the C-FIND response is converted to DICOM+XML, or DICOM+JSON is based on the specification in the Accept types in the initial HTTP/HTTPS request.

Processing logic also optionally caches the C-FIND response (processing block 513). Processing logic sends the reformatted C-FIND response to the remote web client (processing block 514). In one embodiment, sending the reformatted C-FIND response may comprise batching the response until after all C-FIND messages are received and returning them as one response of known size. In another embodiment, sending the reformatted C-FIND response comprises streaming the QIDO-RS response, returning a formatted (e.g., DICOM+XML or DICOM+JSON) data chunk after each C-FIND message.

WADO-RS with C-GET Workflow

In one embodiment, the WADO-RS with C-GET workflow begins after a WADO-RS request is issued by a remote web client. When the universal web service engine described herein receives a WADO-RS request or, upon parsing the parameters after {SERVICE} in the WADO-RS request, recognizes that the request is WADO-RS, then the universal web service engine creates an internal DICOM SCU client that issues a C-GET request to the <SCP Host> on the <SCP Port> using the AeTitles provided <SCU AET> and <SCP AET>.

Subsequently, the SCP Host (e.g., PACS, VNA server, etc.) generates and sends back a C-GET response. With the C-GET response, the universal web service engine converts each DICOM object to a different transfer syntax if specified by the Accept type(s) of the initial web request. For example, the DICOM Web Services standard specifies that the following can be used as a URL parameter to request medical DICOM images encoded with JPEG 2000 Lossy compression:

accept=multipart/related;type="application/octet-stream; transfer-syntax=1.2.840.10008.1.2.4.91"

In an alternative embodiment, the desired transfer syntax is included in the C-GET request if supported by the remote PACS. In one embodiment, if the initial URL in the web services request supplied a frame list, as per NEMA standard PS3.18, then the universal web service engine extracts the requested frames. In an alternative embodiment, the desired frame numbers are included in the C-GET request if supported by the remote PACS.

In one embodiment, the universal web service engine renders each DICOM object for display if requested by the initial URL, as per NEMA standard PS3.18, in the original web services request from the web client. For example and not by way of limitation:

http://{SERVICE}/studies/999.083000/series/
999.083000.5/instances/999.083000.5.104/
rendered?accept=image/jpeg In one embodiment, the universal web service engine extracts bulk data if requested by the initial web request from the web client, as per DICOM Web Services PS3.18 6.1.1.8 and 6.5.1.2.2. In one embodiment, the universal web service engine extracts DICOM header information and creates a metadata response in DICOM+XML, or DICOM+JSON or other format requested by the web request's Accept type(s). For example and not by way of limitation:

http://{SERVICE}/studies/999.083000/metadata

In one embodiment, the universal web service engine caches the DICOM objects or rendered DICOM images for faster response on repeated requests for the same healthcare content.

In one embodiment, the universal web service engine wraps each reformatted response item to be returned as an HTML body part as specified by the NEMA standard PS3.18 and returns this response to the remote client. In one embodiment, the universal web service engine batches the C-GET responses and returns the entire reformatted WADO-RS response as one body of known size. In an alternative embodiment, each reformatted response item (e.g. DICOM object, rendered image or frame, bulk data item, metadata) is chunked or streamed back to the remote client as C-GET response objects are received and processed.

Figure 6:
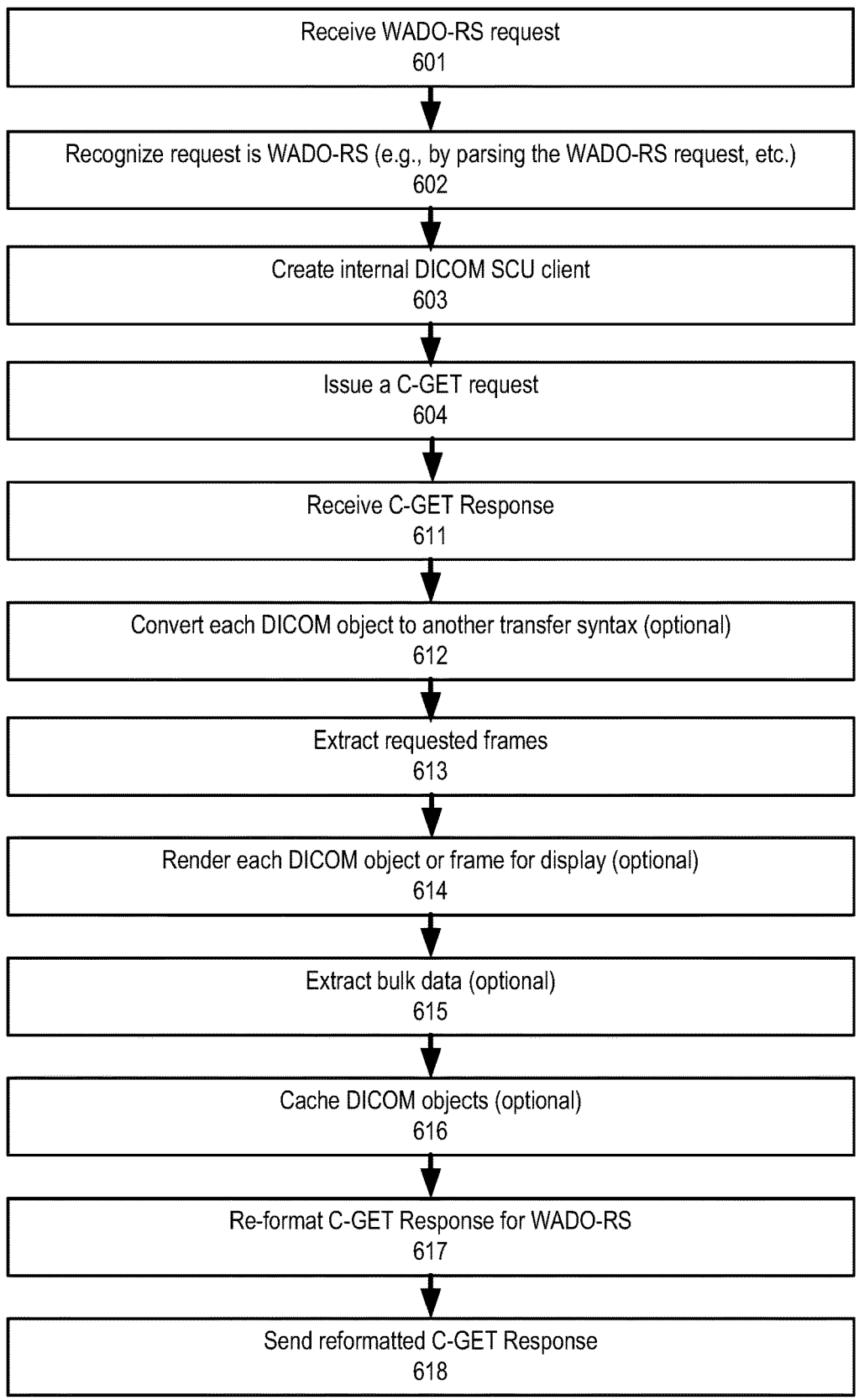
FIG. 6 is a flow diagram of one embodiment of a process for handling a WADO-RS web services request.

FIG. 6 is a flow diagram of one embodiment of a process for handling a WADO-RS web services request using C-GET. In one embodiment, the process is performed by processing logic that may comprise hardware (circuitry, dedicated logic, etc.), software (e.g., software running on a chip), firmware, or a combination of the three. In one embodiment, the process is performed by a medical image management platform, such as, for example, but not limited to, the medical image management platforms described above in conjunction with FIGS. 2 and 3.

Referring to FIG. 6, the process begins by processing logic receiving a WADO-RS request (processing block 601). In one embodiment, the WADO request is received by a universal access (web service) engine. In response to the WADO-RS request, processing logic (processing block 602) recognizes the request is WADO-RS. In one embodiment, processing logic recognizes the request is WADO-RS by parsing the WADO-RS request for a web services identifier. In one embodiment, the web service is identified by parsing that occurs after {Service}. In response to recognizing the request is WADO-RS, processing logic creates an internal DICOM SCU client 603 and issues a C-GET request (processing block 604) that is sent to the PACS/VNA/DICOM server (e.g., SCP host) identified within the original WADO-RS web services request.

Subsequently, processing logic receives a C-GET response from a PACS or VNA or DICOM server (processing block 611). In response to the C-GET response, processing logic can perform a number of operations. In one embodiment, processing logic converts each DICOM object to another transfer syntax (optional) (processing block 612). In one embodiment, if the initial URL specified a frame list, as per NEMA standard PS3.18, then the requested frames may be extracted as part of the conversion process (processing block 613). In one embodiment, processing logic renders each DICOM image or frame for display (e.g. JPEG, PNG) if requested by the initial web request as per a standard (e.g., the NEMA PS3.18) (processing block 614). In one embodiment, processing logic extracts bulk data if requested by the initial URL as per a standard (e.g., the NEMA standard PS3.18) (processing block 615). In one embodiment, processing logic extracts DICOM header information from each DICOM object and creates a metadata response in DICOM+XML, or DICOM+JSON or other format requested by the web request's Accept type(s). In still yet another alternative embodiment, processing logic caches DICOM objects or rendered images (optional) (processing block 616). Cached content allows for faster response on repeated requests for the same medical data.

Processing logic reformats the C-GET response (processing block 617) to satisfy the WADO-RS response format. In one embodiment, processing logic wraps each response items (DICOM objects, frames, rendered displays, bulk data, metadata) with an HTML body part as specified by a standard (e.g., the NEMA standard PS3.18). Then the processing logic sends the reformatted C-GET response to the web client that originally sent the WADO-RS request (processing block 618). In one embodiment, the response could be batched and returned as one HTML object of known size. In another embodiment, the response is chunked or streamed as response items become available.

WADO-RS with C-MOVE

In one embodiment, the WADO-RS with C-MOVE workflow begins after a WADO-RS request is issued by a remote web client (e.g., SCU). When the universal web service engine described herein receives a WADO-RS request or, upon parsing the parameters after {SERVICE} in the WADO-RS request, recognizes that the request is WADO-RS, then the universal web service engine creates an internal DICOM SCU client that issues a C-MOVE request to the <SCP Host> on the <SCP Port> using the AeTitles provided <SCU AET>, <SCP AET> and <DEST AET> and the C-MOVE request is sent to the SCP host.

Subsequently, the SCP Host (e.g., PACS, VNA, server, etc.) generates and sends back a C-MOVE response. With the C-MOVE response, in one embodiment, the universal web service engine provides an internal DICOM SCP to process the C-STORE response from the C-MOVE. The C-STORE DICOM objects may be processed immediately as described below. After processing the C-STORE DICOM objects may be cached or discarded.

In one embodiment, the universal web service engine converts each C-STORE DICOM object to another transfer syntax if specified by the Accept type(s) of the initial web request as described herein with the C-GET workflow. In an alternative embodiment, the requested transfer syntax is specified in the C-MOVE request if supported by the remote PACS. In one embodiment, if the initial URL in the web services request supplied a frame list, as per NEMA standard PS3.18, then the universal web service engine extracts the requested frames from the C-STORE DICOM objects. In an alternative embodiment, the requested frames are specified in the C-MOVE request if supported by the remote PACS.

In one embodiment, the universal web service engine renders each C-STORE DICOM object for display if requested by the initial web request, as per NEMA standard PS3.18, and as described herein under the C-GET workflow. In one embodiment, the universal web service engine extracts bulk data if requested by the initial URL of the web request, as per NEMA standard PS3.18. In one embodiment, the universal web service engine extracts DICOM header information from each DICOM object and creates a metadata response in DICOM+XML, or DICOM+JSON or other format requested by the web request's Accept type(s). In one embodiment, the universal web service engine caches the DICOM objects or rendered images for faster response on repeated requests for same healthcare content.

In one embodiment, the universal web service engine wraps each response item as an HTML body part as specified by the NEMA standard PS3.18 and as described herein under C-GET workflow. The re-formatted C-MOVE response is sent to the remote client as a WADO-RS response. In one embodiment, the universal web service engine batches and returns the entire C-MOVE response as one html object of known size. In another embodiment, the response is chunked or streamed as DICOM objects are processed and response items become available in a manner similar to the C-GET workflow described above.

Figure 7:
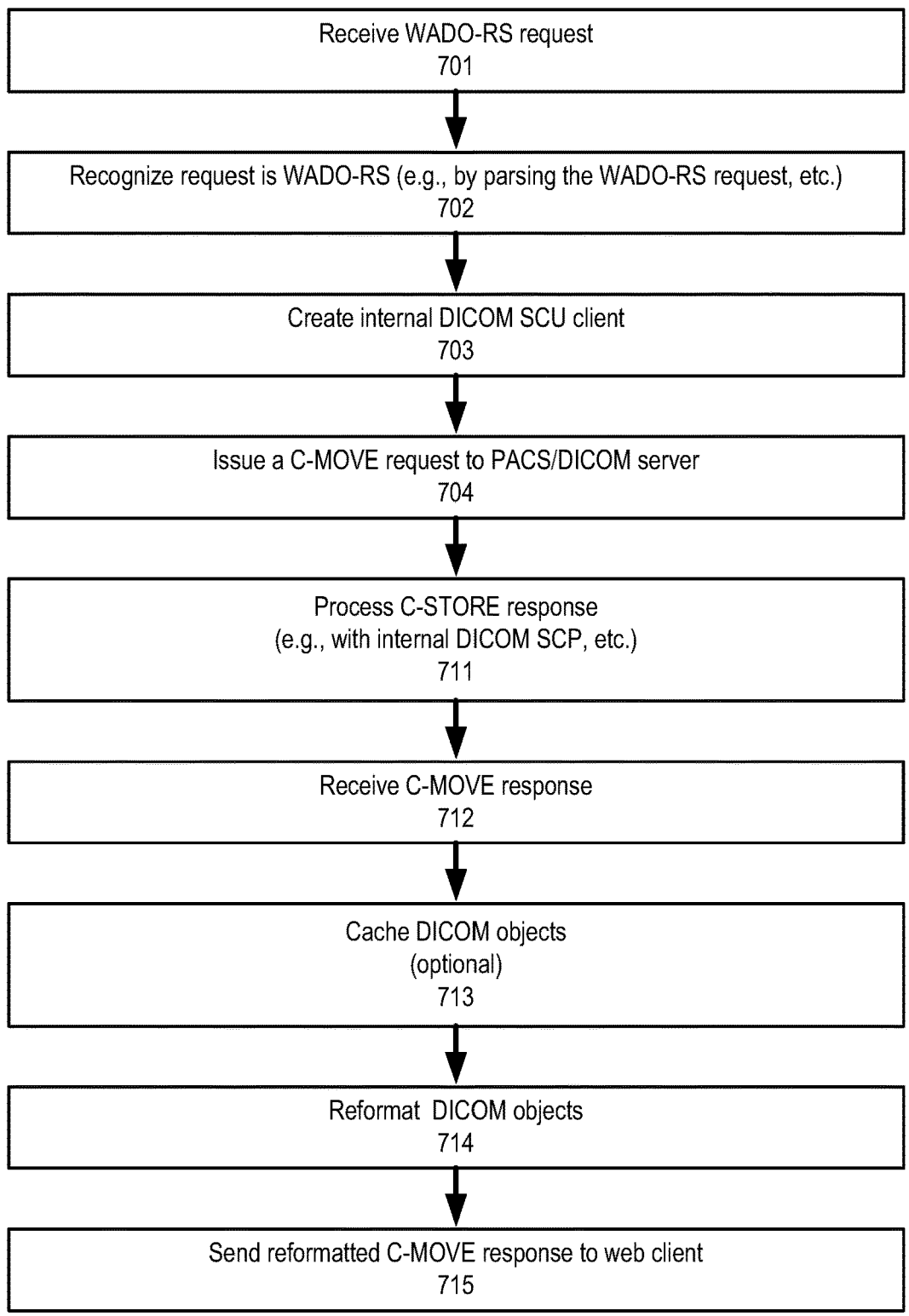
FIG. 7 is a flow diagram of one embodiment of a process for handling a WADO-RS web services request.

FIG. 7 is a flow diagram of one embodiment of a process for handling a WADO-RS web services request using C-MOVE. In one embodiment, the process is performed by processing logic that may comprise hardware (circuitry, dedicated logic, etc.), software (e.g., software running on a chip), firmware, or a combination of the three. In one embodiment, the process is performed by a medical image management platform, such as, for example, but not limited to, the medical image management platforms described above in conjunction with FIGS. 2 and 3.

Referring to FIG. 7, the process begins by processing logic receiving a WADO-RS request (processing block 701). In one embodiment, the WADO request is received by a universal access (web service) engine. In response to the WADO-RS request, processing logic recognizes the request is WADO-RS (processing block 702). In one embodiment, processing logic recognizes the request is WADO-RS by parsing the {Service} part of the URL. In one embodiment, service recognition parsing also includes the URL after {Service}. In response to recognizing the request is WADO-RS, processing logic creates an internal DICOM SCU client 703 and issues a C-MOVE request (processing block 704) that is sent to the PACS/VNA/DICOM server (e.g., SCP host) identified by the original WADO-RS {Service} request.

Subsequently, processing logic processes a C-STORE request from the SCP Host in response to the C-MOVE request (processing block 711). In one embodiment, a DICOM SCP client, internal to the processing logic, receives each C-STORE response for further processing. An SCP client can be created using third party DICOM libraries or built in software following specifications in DICOM standard PS3.1. In one embodiment, processing logic also caches the DICOM objects received as part of the C-STORE response (optional) (processing block 713). The processing logic will receive a C-MOVE response indicating the conclusion of all C-STORE objects sent (processing block 712). In an alternative embodiment, an external SCP client or PACS or VNA may receive and store/cache the C-STORE DICOM objects. In this instance, after receiving the C-MOVE completion response, the processing logic acquires the WADO-RS requested DICOM objects by accessing the external SCP PACS (via DIMSE or Web Services) or external SCP storage or external SCP cache or external SCP data base.

Processing logic reformats the received DICOM objects (processing block 714) and sends the reformatted response to the web client that originally generated the WADO-RS web services request (processing block 715).

WADO-URI Workflow

In one embodiment, workflow for a WADO-URI web request is implemented in the same manner as the workflow for WADO-RS with C-GET or C-MOVE as above with three changes. First, there is only one DICOM object or frame per URL response. Second, the web response is the entire html body. In one embodiment, multi-part body boundaries are not used with WADO-URI. Third, WADO-URI does not support bulk data requests for elements of the DICOM header.

STOW-RS Workflow

In one embodiment, the STOW-RS workflow begins after a STOW-RS request is issued by a remote web client. When the universal web service engine described herein receives a STOW-RS request or, upon parsing the parameters after {SERVICE} in the WADO-RS request, recognizes that the request is WADO-RS, then the universal web service engine creates an internal DICOM SCU client that converts each DICOM instance from the STOW body input to a DICOM object suitable for C-STORE and issues a C-STORE request to the <SCP Host> on the <SCP Port> using the AeTitles provided <SCU AET> and <SCP AET>. Depending on the DICOM transfer syntax negotiation, it may be necessary to convert the transfer syntax of DICOM objects to a format supported on the remote PACS. The universal web service engine sends each DICOM object to the remote PACS/VNA/DICOM server (e.g., SCP host) using DIMSE C-STORE.

Subsequently, the SCP Host (e.g., PACS, VNA, server, etc.) generates and sends back a DIMSE response indicating success or failure of the storage request. The universal web service engine responds to the web client with the C-STORE status converted to a STOW status as per the NEMA standard PS3.18 6.6.1.3.2 "Response Message Body".

Figure 8:
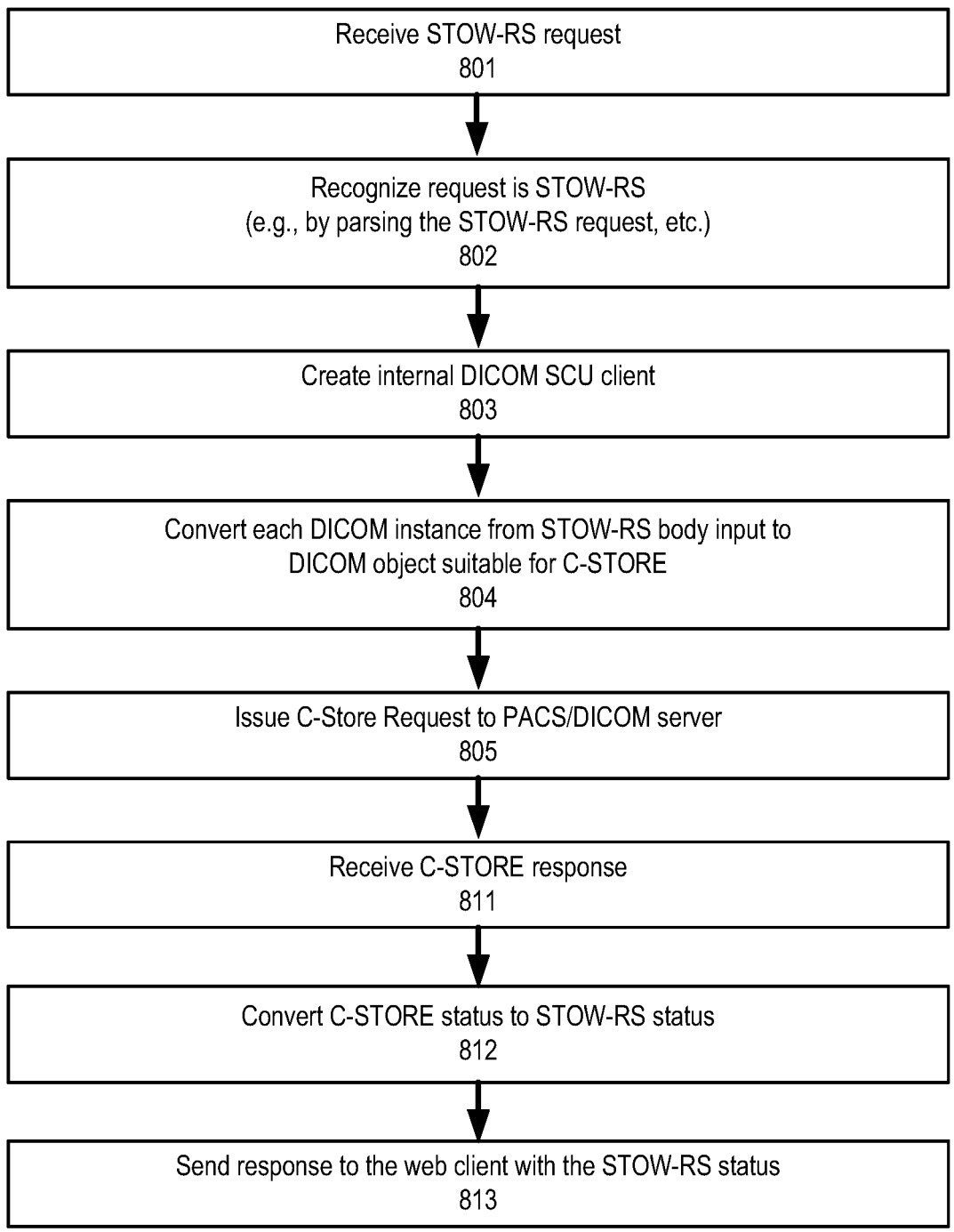
FIG. 8 is a flow diagram of one embodiment of a process for handling a STOW-RS web services request.

FIG. 8 is one embodiment of a process for handling a STOW-RS web services request. In one embodiment, the process is performed by processing logic that may comprise hardware (circuitry, dedicated logic, etc.), software (e.g., software running on a chip), firmware, or a combination of the three. In one embodiment, the process is performed by a medical image management platform, such as, for example, but not limited to, the medical image management platforms described above in conjunction with FIGS. 2 and 3.

Referring to FIG. 8, the process begins by processing logic receiving a STOW-RS request (processing block 801). In response to receiving the STOW-RS request, processing logic recognizes the request is a STOW-RS (processing block 802). In one embodiment, processing logic recognizes the request is STOW-RS by parsing the STOW-RS {SER- VICE} for a service identifier. In one embodiment, processing logic also parses the parameters after {SERVICE}.

In response to recognizing the request as STOW-RS, processing logic creates an internal DICOM SCU client (processing logic 803) and converts each DICOM instance from the STOW body input to a DICOM object suitable for the C-STORE operation (processing block 804). For example, in one embodiment, DICOM header data in DICOM+XML, or DICOM+JSON format is converted to DICOM elements, bulk or binary content that STOW-RS identifies as a metadata link is matched to and replaced by a STOW-RS body part containing the bulk data, and referenced bulk data that is not included in the STOW-RS request is acquired by processing logic making a separate web request for the bulk data using the URL link provided by STOW-RS. In one embodiment, depending on the DICOM transfer syntax negotiation, processing logic may convert the transfer syntax of DICOM objects to a format supported by the remote PACS/VNA/DICOM server. Thereafter, for each successfully assembled and formatted DICOM object, processing logic issues a C-STORE request to the PACS/VNA/DICOM server (e.g., SCP host) identified by the original STOW-RS web services request (processing block 805).

Subsequently, processing logic a C-STORE status response (processing block 811). In response to receiving the C-STORE status response, processing logic converts the C-STORE status to STOW-RS status (processing block 812) and sends the response to the web client with the STOW-RS status (processing block 813).

The workflow discussed above may be useful to apply in number of situations. For example, when developing a vendor neutral DICOM application that queries and displays DICOM content from multiple PACS, one implementation is to use WADO-RS/QIDO-RS with simple authentication schemas like Windows User ID to access PACS vendors. Without the universal access engine described herein some vendor PACS could not be supported using client issued DICOM Web Services. For example, a vendor_1 that is not fully PS3.18 compliant and requires custom fields or headers in the web request or custom formatting of the responses. Another example is a vendor_2 with custom web service authentication like a SSO cookie token created via a web-based form with manual entry of username and password. The desired DICOM application would not be universal or vendor neutral if code is added for vendor specific formats or authentication systems. In addition, a vendor_3 might not yet support DICOM web services but relies instead upon the older DIMSE DICOM messaging.

With the Universal Web Service software, the DICOM application can access Vendor_1, Vendor_2 and Vendor_3 by making WADO-RS/QIDO-RS to the Universal Web Service software. For example:

{Vendor_1 SERVICE}=http://universalHost/myScuAET/Vendor1AET/Vendor1Host/105

Using the workflows described herein, the DICOM application can interact with vendors_1, _2 and _3 using only WADO-RS and QIDO-RS from within the application.

Alternative Schema Embodiments

There are a number of alternatives for the URL schema presented above. In one embodiment, the universal web service engine determines one or more parameters for the DIMSE request by obtaining these parameters from memory using the one or more datums in the original web request. For example, and not by way of limitation, the one or more datums comprise a source name in the web services request. The universal web service engine performs a look up into memory (e.g., a look up table) using the source name to obtain the DICOM server, port and AeTitles for the DIMSE request. Other types of information may be retrieved from memory based on datums in the web service requests. For example the source name lookup may indicate that the source PACS is now DICOM web services compliant and can be accessed directly with QIDO-RS and WADO-RS. In this case the lookup provides an alternative {SERVICE2} value for the vendor, and processing logic replaces the original {SERVICE} with {SERVICE2}, then makes a new web request with the modified URL and original http Accept value (if present), and returns the web response from the vendor directly back to the original client.

In one embodiment, a universal DICOM web service that uses a source name and look-up table to identify the remote PACS and remote connection parameters protocol://webhost[:port]/[serviceName]/sourceName/{NEMA PS3.18 parameters} e.g., GET http://myHost:1000/source1/studies

Processing logic determines that this is a QIDO-RS query for vendor source1 that is not PS3.18 compliant and acquires the DIMSE parameters for a C-FIND request to the vendor via data lookup on source1.

| sourceName | host | port | calledAeTitle | callingAeTitle |
|---|---|---|---|---|
| source1 | Host1 | 105 | AeT1 | myAeT |

Note that in an embodiment, the look up column names are arbitrary. The input method and persistence of this table data is arbitrary. For example, in one embodiment, DIMSE parameters could be read from a formatted file, loaded from a registry key, read from a data base, read from a web.config, or hardcoded in the universal access engine, or its application.

The example above can be extended to WADO-RS requests where the C-MOVE workflow is used and a destination AeTitle is required, for example, shown below:

| sourceName | host | port | calledAeTitle | callingAeTitle | destAeTitle |
|---|---|---|---|---|---|
| source1 | Host1 | 105 | AeT1 | myAeT | myDestAeT |

These examples may be modified to identify sources that are DICOM PS3.18 compliant and the lookup data provides a source approved user name and password for web requests, and {SERVICE} values to substitute for Web service requests, for example, as shown below:

| sourceName | userID | password | QIDO-RS-base | WADO-RS-base |
|---|---|---|---|---|
| eFilm1 | eID | ePassword | http://eHost/qidoRS | http://eHost/wadoRS |

In another alternative embodiment, a STOW-RS base URL added to the table.

In yet another alternative embodiment, a WADO-URI base replaces the WADO-RS base or is an additional table column.

In still yet another alternative embodiment, a new column is added to the table and the source specific access method (web service or DIMSE) is determined by the value entered into the table. This column is optional and the access method could follow simple logic like: apply DIMSE if the {SERVICE} base value is not defined for the source lookup.

In another alternative embodiment, the source name datum in the URL is replaced by a unique port allocated to each configured source. For example,
protocol://webhost:port/{NEMA standard PS3.18 parameters}
e.g., http://myHost:1000/studies
with any of the variant lookup tables in related claims where the port acts as the lookup key instead of source name

| inputPort | host | port | calledAeTitle | callingAeTitle |
|---|---|---|---|---|
| 1000 | aHost1 | 104 | aAeT | myAeT |

In another alternative, both the sourceName and inputPort are used to identify the remote PACS/VNA/DICOM server. For example,
protocol://webhost:port/sourceName/{NEMA standard PS3.18 parameters}
e.g., http://myHost:1000/a1/studies/
with a modified table or any of the variant tables where inputPort is added

| sourceName | inputPort | host | port | calledAeTitle | callingAeTitle |
|---|---|---|---|---|---|
| a1 | 1000 | aHost1 | 105 | aAeT | myAeT |
| a1 | 1001 | aHost2 | 104 | a2AeT | myAeT2 |

Figure 9:
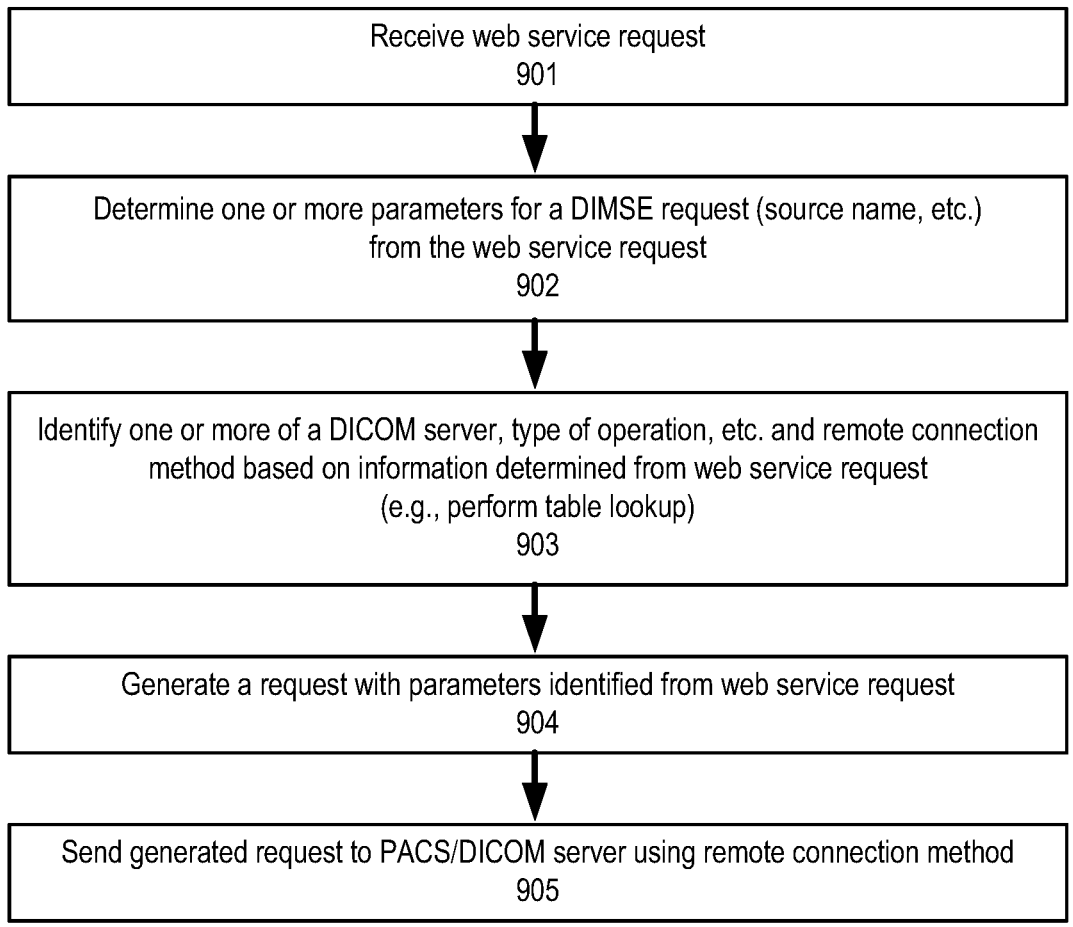
FIG. 9 is a flow diagram of one embodiment of a process for processing a web service request.

FIG. 9 is a flow diagram of one embodiment of a process for processing a web service request using parameters from memory (e.g., a look up table). In one embodiment, the process is performed by processing logic that may comprise hardware (circuitry, dedicated logic, etc.), software (e.g., software running on a chip), firmware, or a combination of the three. In one embodiment, the process is performed by a medical image management platform, such as, for example, but not limited to, the medical image management platforms described above in conjunction with FIGS. 2 and 3.

Referring to FIG. 9, the process begins by processing logic receiving the web service's request (processing block 901) and determining one or more look up keys for a source look up table (processing block 902). In one embodiment, the one or more URL input parameters may comprise a source name and/or port.

Processing logic identifies the service request type from the URL and, optionally, determines the type of remote connection method to apply from a look up table using the input parameters from 902. The look up table is used is obtain necessary information to make a new Web service request or new DIMSE request, based on the information determined from 902 (processing block 903). In one embodiment, processing logic identifies DIMSE parameters for the input parameters 902 based on a look up located in memory (e.g., a look up table).

Using the parameters that have been determined 903, processing logic generates a request (processing block 904) and sends the generated request to the PACS/VNA/DICOM server (processing block 905).

An Exemplary Medical Imaging Management System

Figure 10:
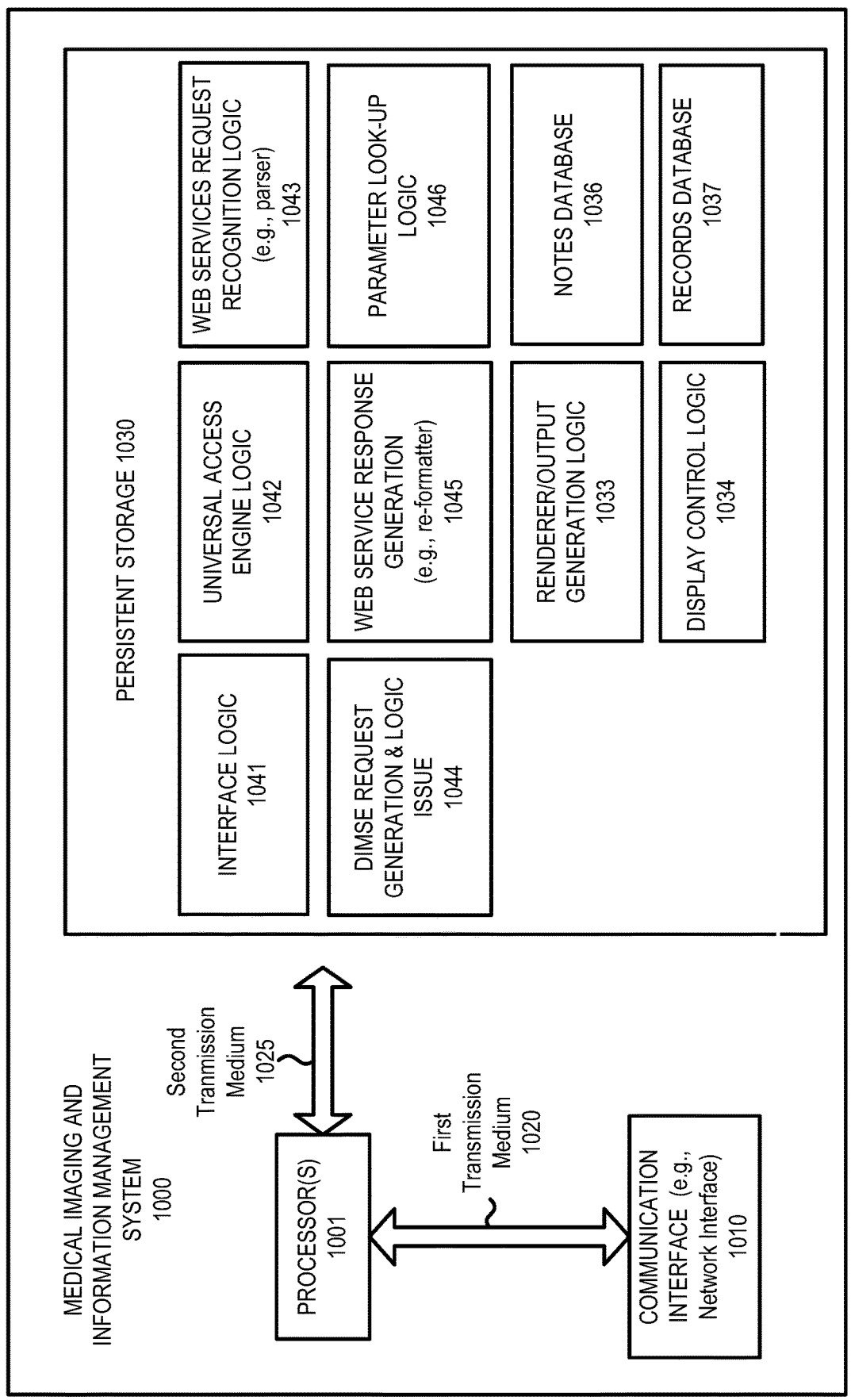
FIG. 10 illustrates an exemplary embodiment of a logical representation of a medical imaging and information management system.

FIG. 10 illustrates an exemplary embodiment of a logical representation of a medical imaging and information management system 1000 that generates and renders layouts with current and prior values of parameters discussed above. In one embodiment, system 1000 is part of a medical image system such as detailed above.

The medical imaging and information management system 1000 includes one or more processors 1001 that are coupled to communication interface logic 1010 via a first transmission medium 1020. The communication interface logic 1010 enables communications with other electronic devices, specifically enabling communication with remote users such as doctors, nurses and/or medical technicians, remote databases (e.g., PACS) that store healthcare studies, healthcare modalities that generate and send studies and one or more remote locations (e.g., cloud-based servers). According to one embodiment of the disclosure, communication interface logic 1010 may be implemented as a physical interface including one or more ports for wired connectors. Additionally, or in the alternative, communication interface logic 1010 may be implemented with one or more radio units for supporting wireless communications with other electronic devices.

Processor(s) 1001 is further coupled to persistent storage 1030 via $2^{nd}$ transmission medium 1025. According to one embodiment of the disclosure, persistent storage 1030 may include data and code to implement: (a) interface logic 1041, (b) universal access engine logic 1042, (c) web services request recognition logic (e.g., parser) 1043, (d) request generation & issue logic 1044, (e) web services response generation (e.g., re-formation) logic 1045, (f) parameter look-up logic 1046, (g) renderer/output generation logic 1033, (h) a display control logic 1034, (i) a notes database 1036 and (j) a records database 1037.

In one embodiment, interface logic 1041 includes logic for enabling interaction between components in the platform, including clients and hosts, as well as between a user and the display areas being displayed on the display screen.

In one embodiment, universal access engine logic 1042 includes logic for enabling the processing and coordination of web services requests and their responses as described above. Web services request recognition logic 1043 includes logic for determining the type of web services that is included in a received web services response. In one embodiment, Web services request recognition logic 1043 includes parsing logic to determine if the web services request includes a web services identifier. DIMSE request generation and issue logic 1044 includes logic to generate and issue a DIMSE request as described above. Web service response generation logic 1045 includes logic to generate a web services response from the response from the DIMSE request received from the SCP host. In one embodiment, web service response generation logic 1045 includes reformatting logic to reformat the response as described above. Parameter look-up logic 1046 includes logic to perform lookups into memory (e.g., a look-up table) to find parameters using information that was included in the web services request so that the parameters may be used in formulating the DIMSE request as described above.

Renderer/output generation logic 1033 includes logic for generating rendered output as described above. Saving the state may include storing, at least, (i) the one or more pieces of information, and (ii) viewing properties of each of the one or more pieces of information in a non-transitory computer-readable medium. The layout template may depict one or more images of a healthcare study that depicts image data that is relevant to a finding from an automated image analysis algorithm.

Display control logic 1034 includes logic for displaying user interfaces, images, DICOM objects, studies or portions thereof, healthcare records that have been rendered locally as discussed above. In one embodiment, display control logic 1034 includes logic to create a browser page into which the images, user interfaces described above, are displayed.

Notes database 1036 stores notes recorded by a doctor, nurse, medical technician, etc., that a user may import into a display area of a layout template. Finally, records database 1037 stores medical records that a user may import into a display area of a layout template.

There is a number of example embodiments described herein.

Example 1 is a method comprising: receiving, at a web service engine, a web services request from a remote web client for one or more Digital Imaging and Communications in Medicine (DICOM) objects; generating a DIMSE service request from the web services request, wherein generating the DIMSE service request includes parsing a modified base URL that includes information for a DIMSE service request, the modified URL being compliant with a standard that specifies a web-based service for accessing and presenting DICOM objects; sending the DIMSE service request to a server; receiving a response to the DIMSE service request from the server; reformatting the response to be compliant with the standard that specifies a web-based service for accessing and presenting DICOM objects; and returning the reformatted response to the remote web client.

Example 2 is the method of example 1 that may optionally include that the modified base URL comprises information necessary for a DICOM C-FIND, C-GET, C-MOVE, or C-STORE request.

Example 3 is the method of example 2 that may optionally include that the standard is the NEMA DICOM Web Services standard PS3.18.

Example 4 is the method of example 1 that may optionally include that the web services request comprises a QIDO-RS, WADO-RS, STOW-RS, or WADO-URI request and the DIMSE service request comprises a DICOM C-FIND, C-GET, C-MOVE or C-STORE operation.

Example 5 is the method of example 1 that may optionally include parsing the web services request after the base URL to identify a type of web service; creating a DICOM client; and issuing, by the DICOM client, one DIMSE service selected based on the type of web service identified.

Example 6 is the method of example 1 that may optionally include that the web services request includes one or more datums, and further comprising determining one or more parameters for the DIMSE request by obtaining the one or more parameters from memory using the one or more datums.

Example 7 is the method of example 6 that may optionally include that the one or more datums are used to determine the connection method for accessing the remote server.

Example 8 is a medical image management system comprising: a network communication interface to receive a web services request from a remote web client for one or more DICOM objects; a memory coupled to the network communication interface to store received healthcare studies; a display screen coupled to the memory to display the received healthcare studies; and one or more processors coupled to the network connection interface, the memory and the display screen and configured to generate a DIMSE service request from the web services request, wherein generating the DIMSE service request includes parsing a modified base URL that includes information for a DIMSE service, the modified URL being compliant with a standard that specifies a web-based service for accessing and presenting DICOM objects, wherein the DIMSE service request is sent to a server via the network communication interface; reformat a response to the DIMSE service request received from the server via the network communication interface; and return the reformatted response to the remote web client via the network communication interface, the response being compliant with the standard that specifies a web-based service for accessing and presenting DICOM objects.

Example 9 is the system of example 8 that may optionally include that the modified base URL comprises information necessary for a DICOM C-FIND, C-GET, C-MOVE or C-STORE request.

Example 10 is the system of example 9 that may optionally include that the standard is the NEMA DICOM Web Services standard PS3.18.

Example 11 is the system of example 8 that may optionally include that the web services request comprises a QIDO-RS, WADO-RS, STOW-RS, or WADO-URI request and the DIMSE service request comprises a C-FIND, C-GET, C-MOVE or C-STORE operation.

Example 12 is the system of example 8 that may optionally that the one or more processors are configured to parse the web services request after the base URL to identify a type of web service; create a DICOM client; and issue, using the DICOM client, one DIMSE service selected based on the type of web service identified.

Example 13 is the system of example 8 that may optionally that the web services request includes one or more datums, and the one or more processors are operable to determine one or more parameters for the DIMSE request by obtaining the one or more parameters from memory using the one or more datums.

Example 14 is the system of example 13 that may optionally that the one or more datums are used to determine the connection method for accessing the remote server.

Example 15 is a non-transitory computer readable storage media having instructions stored thereupon which, when executed by a system having at least a processor, a memory and a display screen therein, cause the system to perform a method comprising: receiving, at a web service engine, a web services request from a remote web client for one or more Digital Imaging and Communications in Medicine (DICOM) objects; generating a DIMSE service request from the web services request, wherein generating the DIMSE service request includes parsing a modified base URL for a service that includes information for a DIMSE service, the DEVISE service request being compliant with a standard that specifies a web-based service for accessing and presenting DICOM objects; sending the DIMSE service request to a server; receiving a response to the DIMSE service request from the server; reformatting the response to be compliant with the standard that specifies a web-based service for accessing and presenting DICOM objects; and returning the reformatted response to the remote web client.

Example 16 is the computer readable storage media of example 15 that may optionally that the standard is the NEMA DICOM Web Services standard PS3.18, and further wherein the modified base URL includes information necessary for a DICOM C-FIND, C-GET, C-MOVE or C-STORE request.

Example 17 is the computer readable storage media of example 15 that may optionally that the web services request comprises a QIDO-RS, WADO-RS, STOW-RS, or WADO-URI request and the DEVISE service request comprises a DICOM C-FIND, C-GET, C-MOVE or C-STORE operation.

Example 18 is the computer readable storage media of example 15 that may optionally that the method further comprising: parsing the web services request after the base URL to identify a type of web service; creating a DICOM client; and issuing, by the DICOM client, one DIMSE service selected based on the type of web service identified.

Example 19 is the computer readable storage media of example 15 that may optionally that the web services request includes one or more datums, and the method further comprises determining one or more parameters for the DIMSE request by obtaining the one or more parameters from memory using the one or more datums.

Example 20 is the computer readable storage media of example 19 that may optionally that the one or more datums are used to determine the connection method for accessing the remote server.

Example 21 is a medical image management system comprising: a network interface to communicate with one or more clients and one or more remote servers; and an access engine, having circuitry, to receive a first set of requests from the one or more clients that are directed to the one or more remote servers, and to issues a second set of requests to the remote servers in response to the first set of requests, the second set of requests being either a DICOM web service request or a DIMSE request.

Example 22 is the medical image management system of example 21 that may optionally that the DICOM web service request comprises a QIDO-RS, WADO-RS, STOW-RS, or WADO-URI request and the DIMSE request comprises a DICOM C-FIND, C-GET, C-MOVE or C-STORE operation.

Example 23 is the medical image management system of example 21 wherein at least one of the first set of requests includes one or more datums, and the access engine is operable to determine whether to use Web Services or DIMSE from one or more datums, and optional persisted data, and the access engine is able to create and issue a valid request to the remote server from one or more datums, and optional persisted data.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices; electrical, optical, acoustical or other form of propagated signals (e.g., carrier waves, infrared signals, digital signals, etc.); etc.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims which in themselves recite only those features regarded as essential to the invention.

We claim:

1. A method comprising:
receiving, at a web service engine, a web services request from a remote web client for one or more Digital Imaging and Communications in Medicine (DICOM) objects;
generating a DICOM Message Service Element (DIMSE) service request from the web services request, wherein generating the DIMSE service request includes parsing a modified base URL that includes information for a DIMSE service request, the modified URL being compliant with a standard that specifies a web-based service for accessing and presenting DICOM objects;
sending the DIMSE service request to a server;
receiving a response to the DIMSE service request from the server;
reformatting the response to be compliant with the standard that specifies a web-based service for accessing and presenting DICOM objects; and
returning the reformatted response to the remote web client.

2. The method defined in claim 1 wherein the modified base URL comprises information necessary for a DICOM C-FIND, C-GET, C-MOVE, or C-STORE request.

3. The method defined in claim 2 wherein the standard is the NEMA DICOM Web Services standard PS3.18.

4. The method defined in claim 1 wherein the web services request comprises a QIDO-RS, WADO-RS, STOW-RS, or WADO-URI request and the DIMSE service request comprises a DICOM C-FIND, C-GET, C-MOVE or C-STORE operation.

5. The method defined in claim 1 further comprising:
parsing the web services request after the base URL to identify a type of web service;
creating a DICOM client; and
issuing, by the DICOM client, one DIMSE service selected based on the type of web service identified.

6. The method defined in claim 1 wherein the web services request includes one or more datums, and further comprising determining one or more parameters for the DIMSE request by obtaining the one or more parameters from memory using the one or more datums.

7. The method defined in claim 6 wherein the one or more datums are used to determine the connection method for accessing the remote server.

8. A medical image management system comprising:
a network communication interface to receive a web services request from a remote web client for one or more Digital Imaging and Communications in Medicine (DICOM) objects;
a memory coupled to the network communication interface to store received healthcare studies;
a display screen coupled to the memory to display the received healthcare studies; and
one or more processors coupled to the network connection interface, the memory and the display screen and configured to
generate a DICOM Message Service Element (DIMSE) service request from the web services request, wherein generating the DIMSE service request includes parsing a modified base URL that includes information for a DIMSE service, the modified URL being compliant with a standard that specifies a web-based service for accessing and presenting DICOM objects, wherein the DIMSE service request is sent to a server via the network communication interface;
reformat a response to the DIMSE service request received from the server via the network communication interface; and
return the reformatted response to the remote web client via the network communication interface, the response being compliant with the standard that specifies a web-based service for accessing and presenting DICOM objects.

9. The system defined in claim 8 wherein the modified base URL comprises information necessary for a DICOM C-FIND, C-GET, C-MOVE or C-STORE request.

10. The system defined in claim 9 wherein the standard is the NEMA DICOM Web Services standard PS3.18.

11. The system defined in claim 8 wherein the web services request comprises a QIDO-RS, WADO-RS, STOW-RS, or WADO-URI request and the DIMSE service request comprises a C-FIND, C-GET, C-MOVE or C-STORE operation.

12. The system defined in claim 8 wherein the one or more processors are configured to:
parse the web services request after the base URL to identify a type of web service;
create a DICOM client; and
issue, using the DICOM client, one DIMSE service selected based on the type of web service identified.

13. The system defined in claim 8 wherein the web services request includes one or more datums, and the one or more processors are operable to determine one or more parameters for the DIMSE request by obtaining the one or more parameters from memory using the one or more datums.

14. The system defined in claim 13 wherein the one or more datums are used to determine the connection method for accessing the remote server.

15. A non-transitory computer readable storage media having instructions stored thereupon which, when executed by a system having at least a processor, a memory and a display screen therein, cause the system to perform a method comprising:
receiving, at a web service engine, a web services request from a remote web client for one or more Digital Imaging and Communications in Medicine (DICOM) objects;
generating a DICOM Message Service Element (DIMSE) service request from the web services request, wherein generating the DIMSE se ice request includes parsing a modified base URL for a service that includes information for a DIMSE service, the DIMSE service request being compliant with a standard that specifies a web-based service for accessing and presenting DICOM objects;
sending the DIMSE service request to a server;
receiving a response to the DIMSE service request from the server;
reformatting the response to be compliant with the standard that specifies a web-based service for accessing and presenting DICOM objects; and
returning the reformatted response to the remote web client.

16. The computer readable storage media defined in claim 15 wherein the standard is the NEMA DICOM Web Services standard PS3.18, and further wherein the modified base URL includes information necessary for a DICOM C-FIND, C-GET, C-MOVE or C-STORE request.

17. The computer readable storage media defined in claim 15 wherein the web services request comprises a QIDO-RS, WADO-RS, STOW-RS, or WADO-URI request and the DIMSE service request comprises a DICOM C-FIND, C-GET, C-MOVE or C-STORE operation.

18. The computer readable storage media defined in claim 15 wherein the method further comprising:
parsing the web services request after the base URL to identify a type of web service;
creating a DICOM client; and
issuing, by the DICOM client, one DIMSE service selected based on the type of web service identified.

19. The computer readable storage media defined in claim 15 wherein the web services request includes one or more datums, and the method further comprises determining one or more parameters for the DIMSE request by obtaining the one or more parameters from memory using the one or more datums.

20. The computer readable storage media defined in claim 19 wherein the one or more datums are used to determine the connection method for accessing the remote server.

21. A medical image management system comprising:
a network interface to communicate with one or more clients and one or more remote servers; and
an access engine, having circuitry, to receive a first set of requests from the one or more clients that are directed to the one or more remote servers, and to issues a second set of requests to the remote servers in response to the first set of requests, the second set of requests being either a Digital Imaging and Communications in Medicine (DICOM) web service request or a DICOM Message Service Element (DIMSE), request.

22. The medical image management system defined in claim 21 wherein the DICOM web service request comprises a QIDO-RS, WADO-RS, STOW-RS, or WADO-URI request and the DIMSE request comprises a DICOM C-GET, C-MOVE or C-STORE operation.

23. The medical image management system defined in claim 21 wherein at least one of the first set of requests includes one or more datums, and the access engine is operable to determine whether to use Web Services or DIMSE from one or more datums, and optional persisted data, and the access engine is able to create and issue a valid request to the remote server from one or more datums, and optional persisted data.

* * * * *

UNITED STATES PATENT AND TRADEMARK OFFICE
CERTIFICATE OF CORRECTION

PATENT NO. : 10,854,328 B2
APPLICATION NO. : 16/370366
DATED : December 1, 2020
INVENTOR(S) : Kibble et al.

Page 1 of 1

It is certified that error appears in the above-identified patent and that said Letters Patent is hereby corrected as shown below:

In the Claims

Column 26, Line 12: Claim 22, Delete "comprises a DICOM C-GET," and insert -- comprises a DICOM C-FIND, C-GET, --

Signed and Sealed this
Ninth Day of February, 2021

Drew Hirshfeld
*Performing the Functions and Duties of the*
*Under Secretary of Commerce for Intellectual Property and*
*Director of the United States Patent and Trademark Office*